United States Patent
Wohleb et al.

(10) Patent No.: US 8,192,692 B2
(45) Date of Patent: Jun. 5, 2012

(54) COATED CHROMATOGRAPH INJECTION PORT LINER FOR PERFORMING SURFACE SORBENT

(75) Inventors: Robert H. Wohleb, Gig Harbor, WA (US); Martin Okiro, Gig Harbor, WA (US)

(73) Assignee: VICI Gig Harbor Group, Inc., Gig Harbor, WA (US)

( * ) Notice: Subject to any disclaimer, the term of this patent is extended or adjusted under 35 U.S.C. 154(b) by 1423 days.

(21) Appl. No.: 10/563,312

(22) PCT Filed: Sep. 16, 2004

(86) PCT No.: PCT/US2004/030263
§ 371 (c)(1),
(2), (4) Date: Dec. 30, 2005

(87) PCT Pub. No.: WO2005/028061
PCT Pub. Date: Mar. 31, 2005

(65) Prior Publication Data
US 2006/0286677 A1      Dec. 21, 2006

Related U.S. Application Data

(63) Continuation-in-part of application No. 10/663,955, filed on Sep. 16, 2003, now Pat. No. 7,087,437.

(51) Int. Cl.
*G01N 30/16* (2006.01)

(52) U.S. Cl. ............ 422/161; 422/178; 95/89; 73/23.41

(58) Field of Classification Search ............... 422/69, 422/80, 89, 101, 102; 436/161, 175, 178, 436/181; 95/89, 90; 96/105; 73/23.41
See application file for complete search history.

(56) References Cited

U.S. PATENT DOCUMENTS

| | | | |
|---|---|---|---|
| 3,615,272 A | 10/1971 | Collins et al. | |
| 3,958,944 A | 5/1976 | Wong | |
| 3,964,872 A | 6/1976 | Karinkanta | |
| 4,268,481 A | 5/1981 | Suovaniemi | |
| 4,382,000 A | 5/1983 | Wisebaker et al. | |
| 4,565,100 A | 1/1986 | Malinoff | |
| 4,720,351 A | 1/1988 | Flynn et al. | |
| 4,890,502 A * | 1/1990 | Elias et al. ................. | 73/864.85 |
| 4,954,149 A * | 9/1990 | Fullemann ...................... | 96/105 |
| 4,980,294 A * | 12/1990 | Elias et al. ...................... | 436/21 |
| 5,279,742 A | 1/1994 | Markel et al. | |

(Continued)

FOREIGN PATENT DOCUMENTS
WO      WO/00/30753      6/2000

OTHER PUBLICATIONS
Definition of "coating" http://en.wiktionary.org/wiki/coating, Feb. 2, 2009.

(Continued)

*Primary Examiner* — Jan Ludlow
(74) *Attorney, Agent, or Firm* — James E. Hudson, III; Crain, Caton & James, P.C.

(57) ABSTRACT

A sorption liner (100) has a sorbent material coating (150) on an inside surface (106). Sample components are adsorbed on the coating (150), the liner (100) is attached to an analytical device, such as a gas chromatograph, and the components desorbed.

5 Claims, 2 Drawing Sheets

U.S. PATENT DOCUMENTS

| | | | |
|---|---|---|---|
| 5,292,801 A | | 3/1994 | Avnir et al. |
| 5,391,298 A | | 2/1995 | Pieper et al. |
| 5,403,489 A | | 4/1995 | Hagen et al. |
| 5,415,779 A | | 5/1995 | Markell et al. |
| 5,472,600 A | | 12/1995 | Ellefson et al. |
| 5,531,810 A | * | 7/1996 | Fullemann .................. 96/105 |
| 5,565,622 A | | 10/1996 | Murphy |
| 5,595,649 A | | 1/1997 | Markell et al. |
| 5,595,653 A | | 1/1997 | Good et al. |
| 5,599,445 A | | 2/1997 | Betz et al. |
| 5,635,060 A | | 6/1997 | Hagen et al. |
| 5,691,206 A | * | 11/1997 | Pawliszyn .................. 436/178 |
| 5,766,660 A | | 6/1998 | Lee et al. |
| 5,827,944 A | | 10/1998 | Nickershon |
| 5,882,939 A | * | 3/1999 | Kovar et al. .................. 436/162 |
| 5,897,779 A | | 4/1999 | Wisted et al. |
| 5,911,883 A | | 6/1999 | Anderson |
| 5,947,274 A | | 9/1999 | Taskis et al. |
| RE36,811 E | | 8/2000 | Markel et al. |
| 6,095,356 A | | 8/2000 | Rits |
| 6,207,049 B1 | | 3/2001 | Abdel-Rahman |
| 6,287,521 B1 | | 9/2001 | Quay et al. |
| 6,416,716 B1 | | 7/2002 | Shukla et al. |
| 6,537,502 B1 | | 3/2003 | Shukla et al. |
| 7,087,437 B2 | | 8/2006 | Wohleb |
| 2002/0150923 A1 | | 10/2002 | Malik |
| 2004/0147040 A1 | | 7/2004 | Bluggel |
| 2006/0110295 A1 | | 5/2006 | Wohleb |
| 2006/0115383 A1 | | 6/2006 | Wohleb |
| 2006/0115384 A1 | | 6/2006 | Wohleb |
| 2007/0003441 A1 | | 1/2007 | Wohleb |

OTHER PUBLICATIONS

Ludlow, Jan, International Search Report, May 27, 2005, 3 pages, USPTO, US.

Hocquet, Alain, Supplementary European Patent Search, Mar. 20, 2008, 3 pages, European Patent Office, Netherlands.

Ludlow, Jan, International Preliminary Report on Patentability, Aug. 29, 2005, 3 pages, USPTO, US.

Ludlow, Jan, International Search Report—PCT/US04/30263, May 27, 2005, 3 pages, USPTO, US.

Ludlow, Jan, International Preliminary Report on Patentability—PCT/US04/30263, Aug. 29, 2005, 3 pages, USPTO, US.

Ludlow, Jan, Written Opinion of the International Searching Authority—PCT/US04/29143, Dec. 12, 2005, 3 pages, USPTO, US.

Ludlow, Jan, International Preliminary Report on Patentability—PCT/US04/29143, May 12, 2006, 3 pages, USPTO, US.

* cited by examiner

US 8,192,692 B2

COATED CHROMATOGRAPH INJECTION PORT LINER FOR PERFORMING SURFACE SORBENT

CROSS-REFERENCE TO RELATED APPLICATIONS

This application is a continuation-in-part under to U.S. application Ser. No. 10/663,955, "Direct Vial Surface Sorbent Micro Extraction Device and Method," filed on Sep. 16, 2003 by Robert Wohleb now U.S. Pat. No. 7,087,437.

STATEMENT REGARDING FEDERALLY SPONSORED RESEARCH OR DEVELOPMENT

Not Applicable.

BACKGROUND OF THE INVENTION

1. Field of the Invention

This invention relates to the extraction and collection of one or more analytes by a sorption process. Specifically, this invention relates to a device and method for performing extraction and desorption on an analyte-bearing sample.

2. Description of the Related Art

To prepare samples for chemical analysis, often analytes, or the compound of interest, must be separated from a sample matrix, such as water, soil or animal tissue, and presented in a form suitable for a particular piece of analytical equipment, such as a gas or liquid chromatograph. There are various extraction methods known and used to collect and prepare samples for such chemical analysis. These methods include liquid/liquid extraction, solid phase extraction, solid phase microextraction and stir-bar sorptive extraction. The new trend in the industry is toward simplified sample preparation that results in reduced waste and pollutants.

Liquid/liquid extraction partitions an analyte between two immiscible phases, such as an organic solvent and an aqueous phase. When an aqueous phase contains the analyte, the analyte is extracted into the immiscible organic solvent by placing the two phases into contact. Extraction is further enhanced by mixing. A relatively large volume of solvent (typically greater than 100 mL) is necessary to carry out the extraction. Partitioning of a compound between the solution solvent and extractant solvent is governed by the distribution constant, K, and the phase ratio, r. An example of such an extraction would be EPA test method SW846 3510 which specifies that one liter of aqueous sample should be serially extracted with 350 mL of methylene chloride. When the entire procedure is considered, a total of 500 mL of solvent is used for each sample. The solvent extract must be evaporated to reduce its volume to between 1 and 2 mL for placement into an autosampler vial prior to analysis.

Solid phase extraction (SPE) is often used to extract a sample prior to analysis by chromatography. SPE uses silica particles with an organic layer covalently attached to the surface of the particles. The silica particles are packed into a tube or disc, such as a polyethylene syringe barrel. The sample is then prepared and an analyte extracted by passing the sample through the solid sorbent. The analyte is then desorbed from the SPE media by solvent extraction. An example of such an extraction is EPA test method SW846 3535 which utilizes one liter of sample but requires approximately 50 mL of solvents. The solvent extract must be evaporated to reduce its volume to between 1 and 2 mL for placement into an autosampler vial prior to analysis.

It is known in the art to use a sorbent to extract an analyte from a solution. The analyte is later extracted from the sorbent by thermal desorption or by back extracting with a small amount of organic solvent. Sorption materials are usually homogenous, non-porous materials that are above their glass transition point ($T_g$) and in which the analyte can dissolve. The sample may be removed for analysis by thermal desorption or solvent extraction.

Stir-bar sorptive extraction (SBSE) is used primarily for direct mode sampling. SBSE utilizes a thick sorbent coating on a magnetic bar stirrer that stirs the sample for a predetermined amount of time during which time the analyte partitions between the stir-bar sorbent and the sample. After extraction, the stir-bar is removed and the analyte is thermally desorbed to the injection port of a gas chromatograph.

Examples of the prior art follow:

U.S. Pat. No. 5,391,298 issued to Pieper et al. on Feb. 21, 1995 discloses an apparatus that can be used to perform a solid phase extraction under pressurized conditions. The apparatus includes a pressurizable housing with an inlet tube that can communicate with a pump, which feeds a liquid to the housing under positive pressure. A disk assembly includes fluid-permeable, porous sheets on opposite sides of an SPE membrane.

U.S. Pat. No. 5,691,206, issued to Pawliszyn on Nov. 25, 1997 discloses a device for carrying out solid phase microextraction. The device is a fiber, solid or hollow, contained in a syringe. The syringe has a barrel, a plunger slidable within the barrel and a hollow needle extending from the end of the barrel opposite the plunger. The needle contains the fiber. When the plunger is depressed, the fiber extends beyond a free end of the needle find when the plunger is in a withdrawn position the fiber is located within the needle. To collect a sample, the needle is inserted through a septum in a bottle containing the sample and the fiber is extended into the sample. After a predetermined amount of time, the fiber is returned to the needle and the syringe is withdrawn from the bottle. The sample is analyzed by inserting the needle through a septum in a gas injection port of a gas chromatograph and extending the fiber.

U.S. Pat. No. 5,565,622, issued to Murphy on Oct. 15, 1996 discloses a simplified method for solid phase extraction of components of interest from a sample. A syringe is used in which the inner surface of the cannula or needle is at least partially coated with a stationary phase such that aspirating the sample into the needle results in adsorption of the components of interest into the stationary phase. Aspiration of a solvent may be employed for removing the components of interest from the stationary phase for direct injection into a chromatographic instrument, or the components of interest may be removed by thermal desorption, wherein the needle is placed in the injection port of the chromatographic instrument and heated.

U.S. Pat. Application Pub. Ser. No. US 2002/0105923, applied for by Malik, published on Oct. 17, 2002 discloses a method of preconcentrating trace analytes by extracting polar and non-polar analytes through a sol-gel coating. The sol-gel coating is either disposed on the inner surface of the capillary tube or disposed within the tube as a monolithic bed.

U.S. Pat. Application Pub. Ser. No. US 2002/0098594 A1, applied for by Sandra et al., published on Jul. 25, 2002, discloses a method and collector for solid-phase microextraction and analysis. A collector, which contains the sorption phase, is generally a magnetic stir bar, or a glass rod encased by a hose. The collector is brought into contact with a substance for sufficient time and then is subjected to a solid-phase microextraction apparatus. The apparatus comprises a desorption tube that is adjoined to the collector. The apparatus is connected to an analysis device, like a gas chromatograph, and a carrier gas flows through the desorption tube. Substances attached to the collector are desorbed and are passed to the analysis device by the carrier gas. Thus, in order to perform extraction and desorption of an analyte, Sandra et. al. requires excessive equipment and steps.

Canadian Pat. No. 2,280,418, issued to Forsyth on Feb. 12, 2001, discloses a technique for carrying out solid phase microextraction of analytes contained within a liquid, solid or other material. A fiber assembly is mounted in the headspace of a gas-tight container. A coating is applied to the fiber assembly based on selectivity of the coating towards at least one analyte present in the sample. The fiber assembly is exposed either in direct contact with the sample, or indirectly through contact with the gas present in the headspace of the container. After exposure, the analyte-containing fiber is then desorbed so the desired analyte can be analyzed. There are two alternatives for desorption under Forsyth. The coating must be removed from the fiber through solvent swell. Once the coating has been removed, the coating is placed in an autosampler vial containing a portion of solvent. The coating is suspended in the solvent, which can result in contamination and interference with the autosampler. Additionally, while this method reduces the amount of solvent necessary in the prior art, this method still requires a greater amount of solvent than the present invention. Alternatively, the coating can be left on the fiber and the fiber can be placed in the autosampler vial with a portion of solvent. However, this method still presents problems with autosampler contamination and operation.

An article entitled, "Headspace Sorptive Extraction (HSSE)" was published on an unspecified date by Tienpont, B. et al. at http://www.richrom.com/assets/CD23PDF/d43.pdf. The article discloses a glass rod support coated with a sorptive coating and suspended in the headspace of a closed container, which contains the analyte-bearing sample. The glass rod remains suspended above the analyte-bearing sample until equilibrium is reached. The glass rod is then removed from the closed container and undergoes thermal desorption.

It would be an improvement to the art to have a device where the extraction and desorption may be performed without the need of extraneous equipment.

BRIEF SUMMARY OF THE INVENTION

The present invention comprises a device and method for extracting analytes from an analyte-bearing sample. Accordingly, the objects of my invention are to provide, inter alia, a single step solid phase extraction system that:
  eliminates the use of solvent during extraction;
  minimizes the amount of labor required to perform an extraction;
  minimizes the amount of equipment required;
  has greater reproducibility than solid phase micro extraction;
  reduces or eliminates sample cross contamination; and
  does not require expensive thermal desorption equipment.

This invention is a tube with an internal sorptive coating, wherein a steady flow of analyte-bearing sample traverses the internal passageway defined by the internal sorptive coating. Upon exposure to the coating, the desired analytes are extracted from the sample. After an amount of time, equilibrium is reached and extraction is complete. The coated tube is then removed and connected to an analytical device for desorption and analysis.

DESCRIPTION OF THE INVENTION

Figure 1:
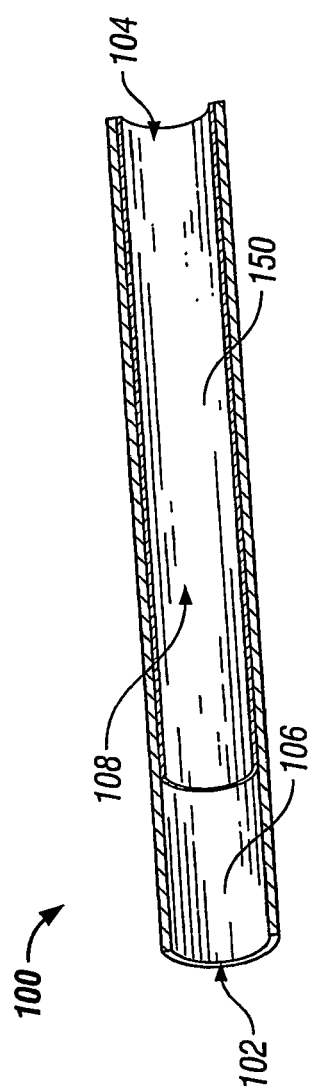
FIG. 1 is a cross-sectional view of the inventive liner with a sorptive coating.

Referring to FIG. 1, the inventive liner is depicted as tubular member 100. A nonreactive material, such as glass, should be used to make tubular member 100. Tubular member 100 is cylindrically shaped, having a hollow interior surface 106, inlet 102, outlet 104, and passageway 108. Passageway 108 is defined by interior surface 106 of tubular member 100, with sorptive coating 150 coating interior surface 106. Sorptive coating 150 coats interior surface 106 without blocking inlet 102 and outlet 104 or clogging passageway 108. Consequently, passageway 108 is unobstructed. Interior surface 106 can either have a uniformly smooth surface or an irregular surface.

When the volume of analyte-bearing sample 250 is greater than the internal volume of tubular member 100, analyte-bearing sample 250 will be continuously fed through tubular member 100 from an outside source (not shown). FIG. 2A depicts tubular member 100 in assembly 300. Assembly 300 connects tubular member 100, sample vessel 200 and pump 320 in a loop, so that analyte-bearing sample 250 may be continuously cycled through system 300. Sample vessel 200 contains analyte-bearing sample 250 and supplies analyte-bearing sample 250 to system 300. When pump 320 is actuated, pressure cyclically pumps analyte-bearing sample 250 from sample vessel 200, through tubular member 100, and back to sample vessel 200. Analyte-bearing sample 250 enters inlet 102 and exits outlet 104. As analyte-bearing sample 250 continuously flows through passageway 108, at least one analyte is extracted. Analyte-bearing sample 250 continues to flow through assembly 300 until equilibrium is reached. This is known as active extraction.

Figure 2B:
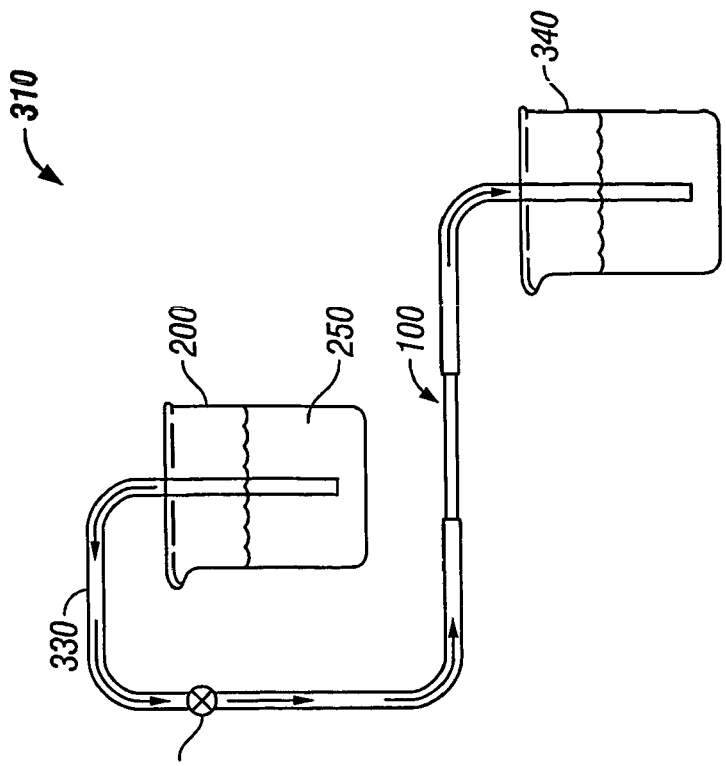
FIG. 2B depicts an alternative large analyte-bearing sample volume assembly, where the inventive liner is connected in series with the analyte-bearing sample and a pump.
Figure 2A:
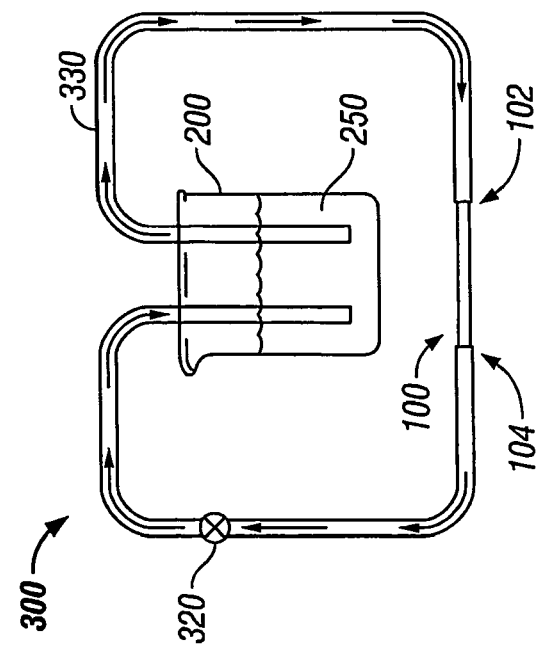
FIG. 2A depicts a large analyte-bearing sample volume assembly, where the inventive liner is connected in loop with the analyte-bearing sample and a pump.

FIG. 2B depicts alternative assembly 310, where analyte-bearing sample 250 flows through alternative assembly 310 for a predetermined period of time. Alternative assembly 310 links sample vessel 200, pump 320, and tubular member 100 in series. Pump 320 is actuated, pumping analyte-bearing sample 250 from vessel 200, through tubular member 100, and terminating at collection vessel 340. Analyte-bearing sample 250 flows through tubular member 100 for a predetermined period of time, during which time at least one analyte is extracted. Once the specified time has elapsed, pump 320 terminates. If equilibrium is not reached before terminating the fluid flow through system 310, passive extraction has been performed.

In both active and passive extraction, the rate of fluid flow can effect the extraction of analytes. In order to achieve reproducible results, a constant flow rate is necessary. The shape of the liner, including length, inside diameter, and irregularity, has an effect on optimum fluid flow rate, which can be determined experimentally.

Figure 3:
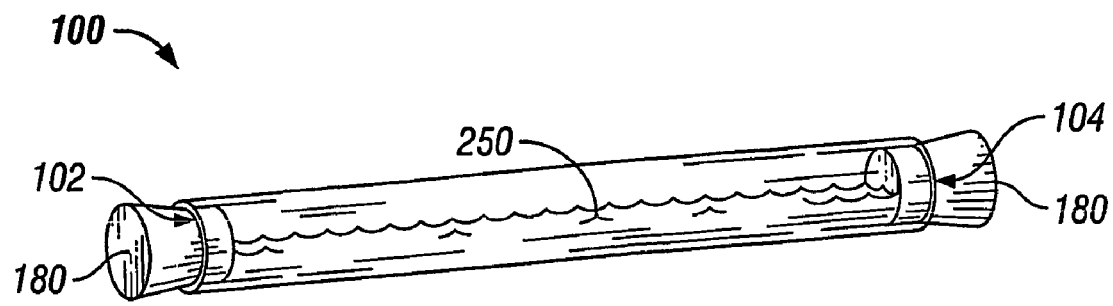
FIG. 3 depicts the inventive liner containing a small volume of analyte-bearing sample.

Assembly 300 and alternative assembly 310 are not practicable when analyte-bearing sample 250 has a volume less than or equal to the internal volume of tubular member 100. Instead, the full volume of analyte-bearing sample 250 is retained within tubular member 100. As depicted in FIG. 3, both inlet 102 and outlet 104 are plugged, with analyte-bearing sample 250 retained within tubular member 100. Plug 180 is inserted into outlet 104, preventing fluid from passing through outlet 104. Analyte-bearing sample 250 is fed to passageway 108, and plug 180 is inserted into inlet 102. Tubular member 100 is then agitated with a mechanical shaker (not shown) for a predetermined period of time, allowing sorptive coating 150 to contact analyte-bearing sample 250 and extract at least one analyte. When the volume of analyte-bearing sample 250 is small, the extraction should occur very rapidly. Plugs 180 are then removed from inlet 102 and outlet 104, releasing the remaining analyte-bearing sample 250.

Figure 4:
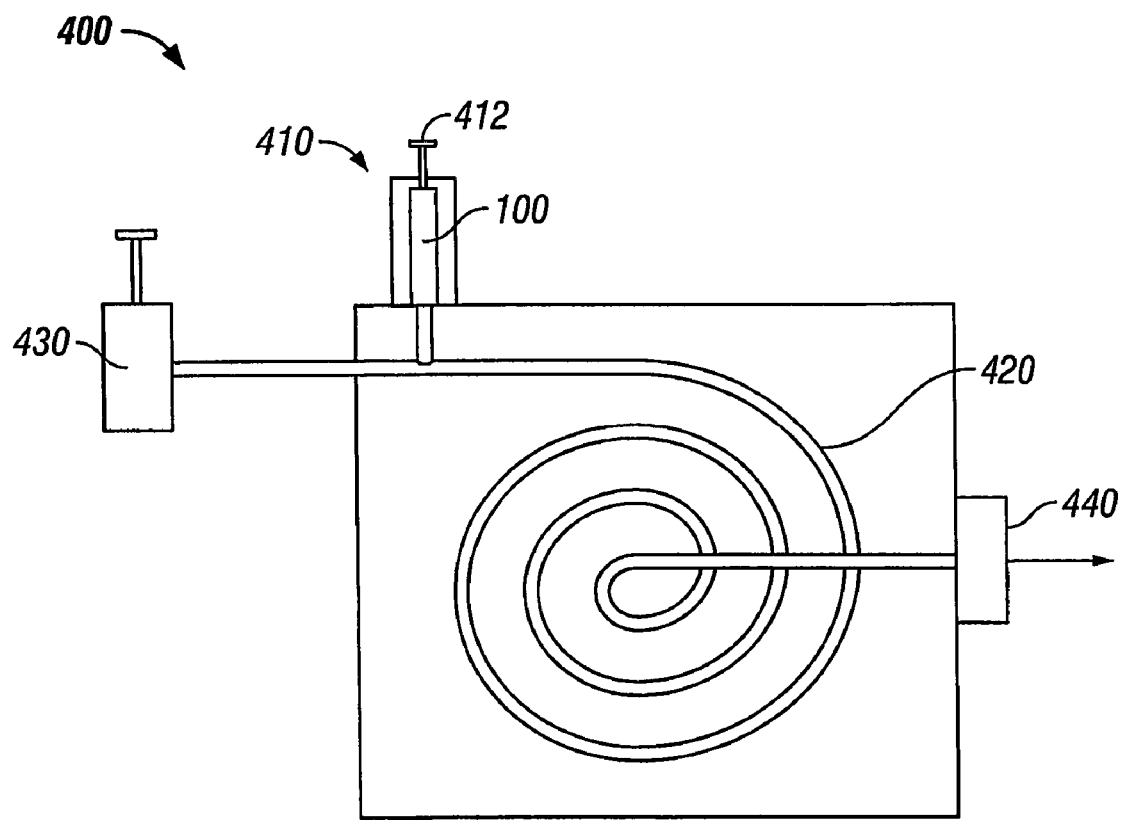
FIG. 4 is a schematic of the inventive liner installed in the injection port housing of a gas chromatograph.

Once tubular member 100 has adsorbed at least one analyte, tubular member 100 is connected to an analytical device. Referring to FIG. 4, tubular member 100 is connected within gas chromatograph 400. In the preferred embodiment, tubular member 100 is sized so that it replaces the standard injection port liner in gas chromatograph 400. Tubular member 100 is installed into injection port housing 410, and provides fluid communication between injection port septum 412 and column 420. Thus, tubular member 100 serves as the injection port liner for gas chromatograph 400. Once gas chromatograph 400 is actuated, gas chromatograph 400 incrementally increases the temperature of injection port housing 410 based on a predetermined rate. After injection port housing 410 reaches a predetermined maximum temperature, gas chromatograph 400 maintains the maximum temperature for injection port housing 410. Throughout this process, analytes present in sorptive coating 150 undergo desorption and enter a gaseous state. In an alternative embodiment, injection port housing 410 may require retrofitting, including adding a cold trap interposed between tubular member 100 and column 420. Desorbed analytes (not shown) are then carried into column 420 by carrier gas 430. Gaseous analytes traverse column 420 and exit gas chromatograph 400 at detector 440.

In the preferred embodiment, the sorptive coating 150 is a hydrophobic coating, such as an immobilized polysiloxane, for example polydimethylsiloxane (PDMS), which contains only methyl functional groups. The name "siloxane" is based on the Si—O—Si unit and has found acceptance in scientific nomenclature. Polysiloxanes are polymers with repeating siloxane units. Each repeating siloxane unit contains two functional groups attached (e.g. dimethyl) which may, or may not, be of the same type of functional group. A functional group is an atom or combination of atoms which gives a polymer its distinctive and characteristic chemistry. A polysiloxane of 50 repeating units would therefore have 100 methyl groups, whereas a siloxane unit with two different types of groups such as phenymethyl would have 50 of each "type" in the polysiloxane.

It is known in the art that immobilized polysiloxanes that contain other types of functional groups, may be used as sorbents. These include immobilized polysiloxanes containing phenyl or trifluoropropyl functional groups. Examples of these polysiloxanes include diphenylsiloxane-dimethylsiloxane copolymers and trifluoropropylmethylsiloxanes. For more selective sorption applications the immobilized polysiloxane may contain other types of functional groups including alkyl, alkenyl, alkynyl, aryl, alkylaryl, alkenylaryl, alkynylaryl, haloalkyl or haloaryl. A polysiloxane may contain said types of functional groups in any combination. The selection of the type of functional groups permits the partitioning of a particular analyte or analyes from the sample The polysiloxane coating may be a polymer, a copolymer or a combination of polymers.

Alternatively, sorptive coating 150 may be (1) a porous layer, such as a derivatized etched surface, (2) other immobilized polymers that are above their glass transition temperatures such as poly butadiene, (3) an immobilized porous polymer, such as divinylbenzene, ethyleneglycoldimethacrylate, and copolymers of divinylbenzene and ethyleneglycoldimethacrylate, polyethyleneimine, acrylonitrile, n-vinyl-2-pyrollidinone or 4-vinyl-pyridine, (4) a sol gel or (5) an immobilized adsorbent such as graphatized carbon black. Sorptive coating 150 may be any one of the coatings described or a combination of two or more of the alternative coatings. The selection of the coating or coatings by one skilled in the art is dependent upon the analyte or analytes to be partitioned from sample.

The foregoing disclosure and description of the invention is illustrative and explanatory thereof. Various changes in the details of the illustrated construction may be made within the scope of the appended claims without departing from the spirit of the invention. The present invention should only be limited by the following claims and their legal equivalents.

What is claimed is:

1. A method for the extraction and desorption of at least one analyte in
    a liquid phase analyte-bearing sample, said method comprising:
    providing a gas chromatograph injection port liner sized to be encapsulated within an injection port housing of a gas chromatograph, said injection port housing having a septum at its first end and a column at its second end, said injection port liner sized to fit within said injection port housing and to provide fluid communication between said septum and said column and having length of substantially the entire length of said injection port housing, said gas chromatograph injection port liner having a passageway therethrough, said gas chromatograph injection port liner having an interior surface defining said passageway;
    coating said interior surface of said gas chromatograph injection port liner with a sorptive coating, said sorptive coating selected to partition said at least one analyte from said liquid phase analyte-bearing sample;
    injecting said liquid phase analyte-bearing sample into said passageway of said coated gas chromatograph injection port liner;
    sorptively extracting said at least one analyte from said liquid phase analyte-bearing sample, leaving a liquid phase remaining analyte-bearing sample;
    removing said liquid phase remaining analyte bearing sample from said coated gas chromatograph injection port liner;
    installing said gas chromatograph injection port liner entirely within said injection port housing of said gas chromatograph;
    desorbing said at least one analyte from said coated gas chromatograph injection port liner; and
    introducing said desorbed at least one analyte into said gas chromatograph.

2. The method of claim 1, wherein said sorptive coating comprises at least one selection from the group consisting of:

(a) an immobilized polysiloxane polymer, having two attached functional groups, wherein the first attached functional group is selected from the group consisting of: alkyl, alkenyl, alkynyl, aryl, alkylaryl, alkenylaryl, alkynylaryl, haloalkyl, and haloaryl, and the second attached functional group is selected from the group consisting of: alkyl, alkenyl, alkynyl, aryl, alkylaryl, alkenylaryl, alkynylaryl, haloalkyl, and haloaryl;
(b) a porous layer;
(c) other immobilized polymers above their glass transition temperature;
(d) an immobilized porous polymer;
(e) a sol gel; and
(f) an immobilized adsorbent.

3. The method of claim 2, wherein:
said injection step includes connecting said coated gas chromatograph injection port liner to a vessel;
said vessel containing said liquid phase analyte-bearing sample; and
said removing step includes separating said coated gas chromatograph injection port liner from said vessel.

4. A method for the extraction and desorption of at least one analyte in a liquid phase analyte-bearing sample for use with a heated gas chromatograph, said chromatograph including an injection port housing, said injection port housing having a septum at its first end and a column at its second end, said method comprising:
providing a gas chromatograph injection port liner sized to be encapsulated within said injection port housing of said heated gas chromatograph as a gas chromatograph injection port liner and to provide fluid communication between said septum and said column and having length of substantially the entire length of said injection port housing,
coating an interior surface of said gas chromatograph injection port liner with a sorptive coating;
injecting said liquid phase analyte-bearing sample into said coated gas chromatograph injection port liner;
sorptively extracting said at least one analyte from said liquid phase analyte-bearing sample, leaving a liquid phase remaining analyte-bearing sample;
removing said liquid phase remaining analyte bearing sample from said coated gas chromatograph injection port liner;
installing said gas chromatograph injection port liner entirely within said injection port housing of said gas chromatograph;
increasing the temperature of injection port housing by heating from said heated gas chromatograph until said at least one analyte is desorbed from said coated gas chromatograph injection port liner; and
introducing said desorbed at least one analyte into said gas chromatograph.

5. The method of claim 4, wherein said sorptive coating is selected to partition at least one analyte from said liquid phase analyte-bearing sample.

* * * * *